United States Patent [19]
Purcell, Jr. et al.

[11] Patent Number: 5,571,099
[45] Date of Patent: Nov. 5, 1996

[54] SIDE FIRING PROBE

[75] Inventors: Earl E. Purcell, Jr., Westfield, Mass.; Ronald E. Hille, East Hartland, Conn.

[73] Assignee: Pioneer Optics Company, Windsor Locks, Conn.

[21] Appl. No.: 437,994

[22] Filed: May 9, 1995

[51] Int. Cl.$^6$ .............................. A61B 17/36; A61N 5/06
[52] U.S. Cl. ................................................ 606/17
[58] Field of Search ........................... 606/14, 15, 16, 606/17; 607/88, 89, 92

[56] References Cited

U.S. PATENT DOCUMENTS

| | | |
|---|---|---|
| 4,592,353 | 6/1986 | Daikuzono . |
| 4,693,244 | 9/1987 | Daikuzono . |
| 4,718,417 | 1/1988 | Kittrell et al. ........................ 606/15 |
| 4,736,743 | 4/1988 | Daikuzono . |
| 5,046,810 | 9/1991 | Steiner et al. . |
| 5,095,889 | 3/1992 | Weissmüller et al. . |
| 5,129,895 | 7/1992 | Vassiliadis et al. ........................ 606/6 |
| 5,133,790 | 7/1992 | Prince . |
| 5,163,935 | 11/1992 | Black et al. . |
| 5,188,634 | 2/1993 | Hussein et al. . |
| 5,242,437 | 9/1993 | Everett et al. . |
| 5,246,436 | 9/1993 | Rowe . |
| 5,254,114 | 10/1993 | Reed, Jr. et al. . |
| 5,257,911 | 11/1993 | Fletcher et al. . |
| 5,267,996 | 12/1993 | Fletcher . |
| 5,282,798 | 2/1994 | Bruse et al. . |
| 5,300,063 | 4/1994 | Tano et al. . |
| 5,343,543 | 8/1994 | Novak, Jr. et al. . |

*Primary Examiner*—Angela D. Sykes
*Assistant Examiner*—Sonya Harris-Ogugua
*Attorney, Agent, or Firm*—Pepe & Hazard

[57] ABSTRACT

A side firing fiberoptic probe has an optical fiber with proximal and distal ends and the cladding is removed from its distal end portion. On the distal end of the core is a transparent reflector of generally cylindrical configuration and it is of larger diameter than and coaxial with the core. The reflector has a planar face at its opposite end which extends at an angle to the axis of the reflector and core. Extending about and sealingly engaged with the fiber distal end portion and the reflector is the cylindrical body portion of a transparent end cap. The cap has a closed end spaced from the planar face of the reflector, and it provides an atmospheric interface between the inner surface of its closed end and the planar face of the reflector and about the unclad distal end portion of the core. Light rays passing through the core fall on the planar face in a generally circular pattern and are reflected thereby at an angle of 50°–90° in a generally conical beam through the reflector and cap.

17 Claims, 2 Drawing Sheets

SIDE FIRING PROBE

BACKGROUND OF THE INVENTION

The present invention relates to fiberoptic devices and, more particularly, to a fiberoptic probe providing a concentrated generally circular pattern of light emission to one side of the tip.

In a number of medical procedures, it is necessary to deliver a concentrated pattern of light to one side of the probe to vaporize and/or coagulate tissue disposed to the side of the tip as it is moved within an organ or a blood vessel. One such procedure is in the treatment of benign prostate hyperplasia where the laser beam enlarges the passage through the prostate gland by vaporizing obstructing tissue.

Prior art devices for this purpose have been of two types:

In a first type, a plastic clad fiber has an angular surface polished on the tip so that the light reflected off the angular surface is projected as a large cone of light over the entire cylindrical surface on the side of the fiber. Much of this light hits the surface at an angle above the critical angle and is reflected back into the fiber to be scattered out of the fiber in the wrong direction. Only the light hitting the center of the cylindrical surface is above the critical angle and passes out of the side of the fiber in the desired direction.

In the second type, a glass clad optical fiber is provided with a relatively thick cladding, and the light is reflected off an angle polished surface and is reflected towards the outer cylindrical surface of the fiber. There is some internal reflection off the cylindrical surface formed by the core/cladding interface, and this light is scattered in the wrong direction. Since the difference in index of refraction between the core and cladding is relatively small, the amount of scatter is not very large and this can be an effective design. Because the cladding is relatively thick, a relatively small cone of light hits the cladding/air interface and gives no reflection. The disadvantage to this approach is that there will be some reflection off the core/cladding interface causing some scatter, and the cost of the glass clad fiber is much higher than the plastic clad fiber.

It is an object of the present invention to provide a novel fiberoptic probe which will emit light in a concentrated pattern at substantially a right angle to the axis of the fiberoptic probe.

It is also an object to provide such a fiberoptic probe which may be fabricated relatively readily and which is relatively long lived and reliable in operation.

Another object is to provide such a fiberoptic probe in which the pattern of light exiting therefrom may be manipulated by rotation and axial movement of the device.

SUMMARY OF THE INVENTION

It has now been found that the foregoing and related objects may be readily attained in a side fire fiberoptic probe which includes an optical fiber with proximal and distal ends and having a core and cladding about the core. A portion of the fiber adjacent the distal end is free from cladding, and on the distal end of the core is a transparent reflector of generally cylindrical configuration, and it is larger diameter than and coaxial with the core. The reflector has a planar face at its opposite end which extends at an angle to the axis of the core and reflector. A transparent end cap having a cylindrical body portion extends about and is sealingly engaged with the fiber distal end portion and the reflector. The cap has a closed end spaced from the planar face of the reflector and it is dimensioned to provide an atmospheric interface between the inner surface of its closed end and the planar face of the reflector and about the unclad distal end portion of the core. As a result, light rays passing through the core fall on the planar face in a generally circular pattern and are reflected at an angle of 50°–90° in a generally conical beam through the cylindrical surface of the reflector and cap.

In one embodiment, the length of the reflector is short so that the planar face extends over essentially the full length of the reflector so that the periphery has only a portion of a cylindrical configuration.

Desirably, the angle of the planar face to the axis of the core is 36°–40°, and the cladding is a synthetic resin. The core, reflector and cap have substantially the same composition, preferably silica glass.

Desirably the cylinder is fused to the end of the core, and the cap is fused to the reflector and has a spheroidal closed end portion.

DETAILED DESCRIPTION OF THE PREFERRED EMBODIMENT

Figure 3:
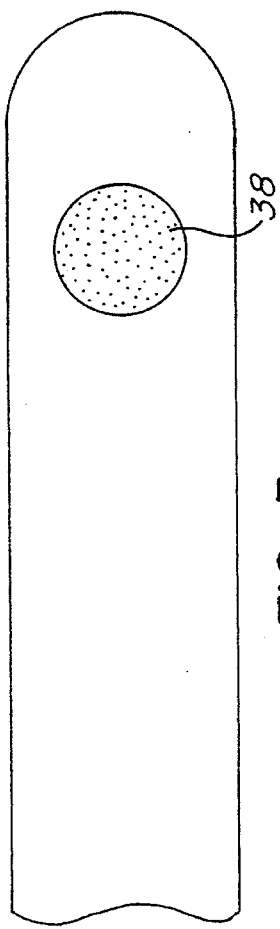
FIG. 3 is a fragmentary top view of the probe showing the light pattern emitted from the fiberoptic probe.
Figure 2:
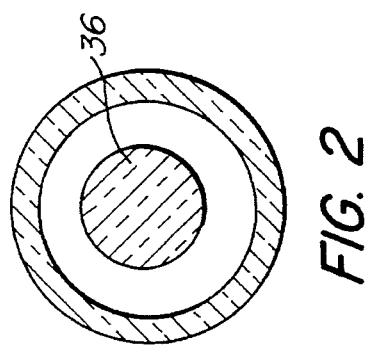
FIG. 2 is a sectional view along the lines 2—2 of FIG. 1 diagrammatically showing the light pattern incident on the reflecting surface.
Figure 1:
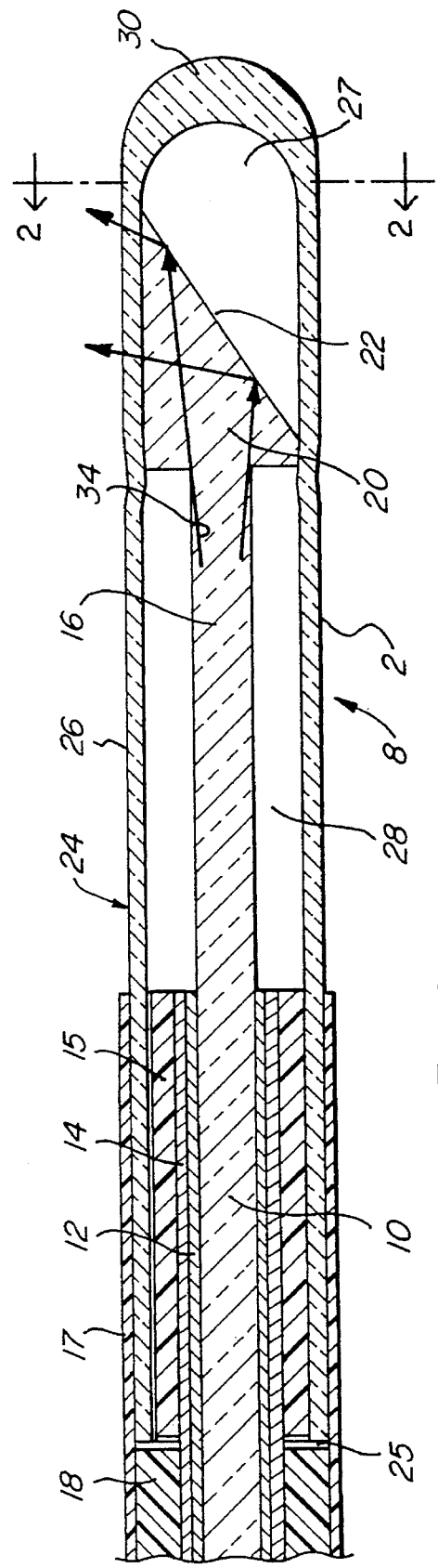
FIG. 1 is a fragmentary sectional view of a fiberoptic delivery probe embodying the present invention with arrows indicating the paths of light rays.

As seen in FIG. 1, a fiberoptic delivery probe embodying the present invention employs a fiberoptic light guide or probe generally designated by the numeral 8 and having a core 10, cladding 12 extending about the core 10, and a buffer layer 14 extending about the cladding 12. The distal end portion 16 of the core 10 is free from cladding 12 and buffer layer 14.

At the distal end of the core 10 is a reflector generally designated by the numeral 20 and having a generally cylindrical configuration of greater diameter than the core 10. The end of the reflector is polished to provide a planar reflecting surface 22 oriented at an angle to the axis of the core 10 and reflector 20.

The reflector 20 is readily fabricated from a cylinder or rod of larger diameter than the core 10, and it is fused to the end of the core 10. The reflector 20 should be of relatively short length so that the light rays 34 which are exiting the core 10 in diverging paths will impinge upon the planar surface 22 over a relatively small area. The diameter of the cylinder 20 is generally 1.5–3, and preferably about 2, times that of the core 10.

At the distal end portion of the probe 8 and the reflector 20 is an elongated cap generally designated by the numeral 24 which has a generally spheroidal tip portion 30 and a cylindrical body portion 26 which also extends over a spacer sleeve 15 on the buffer layer 14 adjacent the distal end thereof. Proximal to the elongated cap is a pliable spacer tube 18 which extends about the buffer layer 14 which has an outside diameter similar to that of the elongated cap 24. This allows thin shrink tubing 17 to be placed over its junction 25 with the proximal end of the elongated cap 24 to effect seal at the junction and eliminate a shoulder. The cap 24 is dimensioned to provide an air space 27 about the reflecting surface 22 as well as an air space 28 about the unclad end portion 16. The cap 24 is sealed to the pliable spacer tube 18, the fiber buffer layer 14, and the spacer sleeve 15 at the junction 25 by an adhesive (not shown).

In operation of the device, light rays travelling down the core 10 are reflected inwardly by the cladding 12 about the core 10 and then by the air interface provided between the unclad distal end portion 16 and cap 24 until they exit the end of the core 10. Those travelling substantially parallel to the axis and those travelling at shallow angles to the axis will impinge upon the planar surface 22 in a generally circular pattern or spot 36, and be reflected at the air interface at substantially a right angle to produce a conical beam represented by the generally circular pattern or spot 38 as the beam exits the top of the elongated cap 24.

Figure 4:
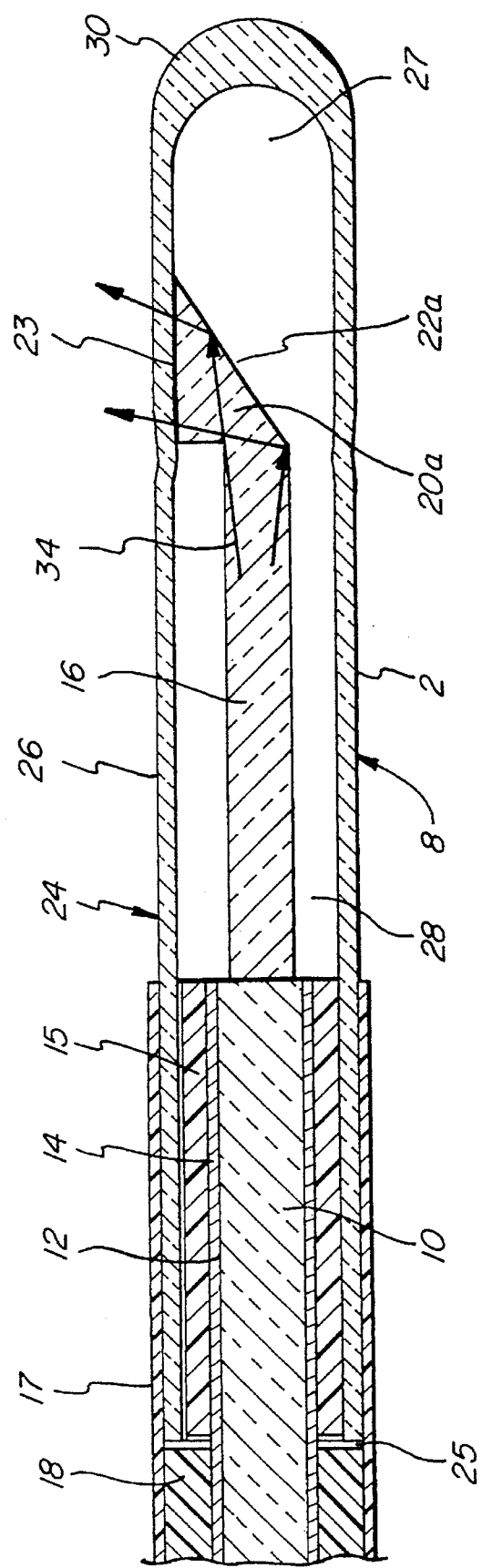
FIG. 4 is a fragmentary sectional view of another embodiment of the probe embodying the present invention.

In FIG. 4, the embodiment is one in which the reflector 20a is of shorter axial length and the planar reflecting surface 22a extends over substantially its entire length. Thus, only a portion 23 of its periphery is cylindrical, and the light rays 34 are refracted by the planar surface 22a through the cylindrical portion 23.

The large diameter cylinder is desirably as short as possible so that a cone of light is projected onto the center of the angled surface. This cone of light reflects off the angle surface, and is projected at substantially a right angle. Since the cone is smaller than the large diameter silica cylinder, the cone is a relatively small spot when it is projected onto the side wall of the elongated cap. This small projection means that none of the light reaches this surface at an angle above the critical angle. Thus, none of the light is reflected back into the fiber to be scattered in another direction (except for Fresnel reflection). In the preferred embodiment, the end of the reflector 20 is polished to provide a planar surface extending at an angle of 36°–40° to the cylindrical axis of the reflector to provide the reflecting surface. This angle causes most of the light rays travelling down the fiber core and into the reflector to strike the planar surface at a 31°–45° angle of incidence (below the critical angle for the silica/air interface) and be totally internally reflected. These light rays will pass outwardly of the reflector and through the cap.

Although the included angle for the planar surface relative to the core may vary from 25°–45°, the preferred angle is about 36°–40°. Some variation is permissible depending upon the desired angle and the concentration desired for the emitted rays.

Similarly, although the preferred configuration for the spheroidal portion of the end of the cap is that of an ellipsoid, a true spherical configuration may also be employed as can be other spheroidal shapes.

In order to avoid undesired differences in indices of refraction and resultant scattering, the composition of the reflector and of the cap should be the same as that of the core. Although various glass compositions may be employed, silica glass has been found to be highly satisfactory. Illustrative of such glass fibers is that sold by Minnesota Mining and Manufacturing Corporation under the designation (FT-600-UMT).

The larger diameter of the reflector relative to the fiber core allows all of the light rays to reach the reflecting surface and be reflected to the output spot. This allows the use of significantly lower cost polymer clad optical fiber.

This design also gives less scattered light than other current designs. In operation, less scatter means less wasted power allowing similar procedures to be done with less power. This design also gives a less divergent, more concentrated output laser beam pattern allowing similar procedures to be done with less laser power. If the fiber does heat up in use, the cap is fused to the fiber with a silica/silica fusion which will be unaffected by tip heating.

As a specific example of a fiberoptic probe embodying the present invention, an optical fiber having a diameter of 600 micrometers supplied by Minnesota Mining and Manufacturing Corporation under the designation FT-600-UMT has its distal end portion stripped by using a fiber buffer strip tool to remove the buffer layer and acetone to remove the cladding. Although only the portion of the core providing the conical tip is required to be free from the cladding and buffer layer, it is desirable to remove the cladding and buffer layer for some distance behind the tip so as to remove these heat sensitive materials from the point of highest output light intensity. The air surrounding the bare core functions as "cladding" to preclude any light egress through the unclad portion adjacent the tip.

A glass cylinder of 1.5 mm in diameter and 2.8 mm in length is fused concentrically to the tip of the core, or the process is conveniently facilitated by using a quartz sleeve to fit over the core. The end of the cylinder is conveniently polished to provide a planar surface disposed at an angle of about 38° to the axis of the core and reflector by use of a series of fine polishing papers such as 40, 30, 10, 5, 3, 1, 0.3 micron grit silicone carbide polishing paper.

The cap is conveniently drawn from a 2 mm outer diameter tube with a wall thickness of about 0.2 mm into a spheroidal tip, and it has an overall length of 15.0 mm. The cap is slid over the reflector and the spacer sleeve. Heat is applied to fuse the cap to the reflector. The proximal end of the cap is sealed to the spacer sleeve, the fiber buffer, and pliable spacer tube using an adhesive sold by Loctite Corporation under the name Loctite 3211.

Thus, it can be seen that the fiberoptic probe of the present invention is one which offers significant advantages in emitting light at a substantially right angle to the axis of the probe and on a concentrated spot. This allows concentration of the emitted light in a small area of the organ or blood vessel being treated. The probe may be fabricated readily and relatively economically, and variation in the pattern and angle of radiation can be effected by minor changes in the angular orientation of the reflector face.

Having thus described the invention, what is claimed is:

1. In a side firing fiberoptic probe, the combination comprising:

(a) an optical fiber with proximal and distal ends having a core and cladding about said core, a portion of said fiber adjacent said distal end being free from cladding;

(b) a transparent reflector of generally cylindrical configuration on the distal end of said core, said reflector being of larger diameter than and coaxial with said core, said reflector having a planar face at its opposite end extending at an angle to said axis of said core and reflector; and (c) a transparent end cap having a cylindrical body portion extending about and sealingly engaged with said fiber distal end portion and said reflector, said cap having a closed end spaced from said planar face of said reflector, said closed end having inner and outer surfaces, said end cap being dimensioned to provide an atmospheric interface between the inner surface of its closed end and said planar face of said reflector and about said unclad distal end portion of said core, whereby light rays passing through said core fall on said planar face in a generally circular pattern and are reflected at an angle of 50°–90° in a generally circular beam through said reflector and cap.

2. A side firing fiberoptic probe in accordance with claim 1 wherein said angle of said planar face to the axis of said core is 25°–45°.

3. A side firing fiberoptic probe in accordance with claim 1 wherein said cladding is a synthetic resin.

4. A side firing fiberoptic probe in accordance with claim 1 wherein said core, reflector and cap have substantially the same composition.

5. A side firing fiberoptic probe in accordance with claim 4 wherein said reflector, core and cap are fabricated from silica.

6. A side firing fiberoptic probe in accordance with claim 1 wherein said cylinder is fused to the distal end of said core.

7. A side firing fiberoptic probe in accordance with claim 5 wherein said cap is fused to said reflector.

8. A side firing fiberoptic probe in accordance with claim 1 wherein said cap has a spheroidal closed end portion.

9. In a side firing fiberoptic probe, the combination comprising:

(a) an optical fiber with a proximal and distal end having a core and synthetic resin cladding about said core, a portion of said fiber adjacent said distal end being free from cladding;

(b) a transparent reflector of generally cylindrical configuration fused to the distal end of said core, said reflector being of larger diameter than and coaxial with said core, said reflector having a planar face at its opposite end of said core extending at an angle to said axis of said core and reflector; and (c) a transparent end cap having an arcuate closed end and a cylindrical body portion sealingly engaged about said fiber distal end portion and said reflector, said cap having a closed end spaced from said planar face of said reflector, said closed end having inner and outer surfaces, said end cap being dimensioned to provide an atmospheric interface between the inner surface of its closed end its end and said planar face of said cylinder and about the unclad distal end portion of said core, whereby light rays passing through said core fall on said planar face in a circular pattern and are reflected at an angle of 50°–90° in a generally circular beam through said reflector and cap.

10. A side firing fiberoptic probe in accordance with claim 9 wherein said reflector, core and cap are fabricated from silica.

11. A side firing fiberoptic probe in accordance with claim 9 wherein said cap has a spheroidal closed end portion.

12. A side firing fiberoptic probe in accordance with claim 9 wherein said core, reflector and cap have substantially the same composition.

13. In a side firing fiberoptic probe, the combination comprising:

(a) an optical fiber with proximal and distal ends having a core and cladding about said core, a portion of said fiber adjacent said distal end being free from cladding;

(b) a transparent reflector on the distal end of said core, said reflector having a peripheral surface including a generally cylindrical portion coaxial with said core and defined by a radius greater than that of said core, said reflector having a planar face at its opposite end extending at an angle to said axis of said core and reflector and generally opposite said cylindrical portion; and (c) a transparent end cap having a cylindrical body portion extending about and sealingly engaged with said fiber distal end portion and said cylindrical portion of said reflector, said cap having a closed end spaced from said planar face of said reflector, said closed end having inner and outer surfaces, said end cap being dimensioned to provide an atmospheric interface between the inner surface of its closed end and said planar face of said reflector and about said unclad distal end portion of said core, whereby light rays passing through said core fall on said planar face in a generally circular pattern and are reflected at an angle of 50°–90° in a generally circular beam through said cylindrical portion of said reflector and cap.

14. A side firing fiberoptic probe in accordance with claim 13 wherein said angle of said planar face to the axis of said core is 25°–45°.

15. A side firing fiberoptic probe in accordance with claim 13 wherein said cladding is a synthetic resin, and said core, reflector and cap have substantially the same composition.

16. A side firing fiberoptic probe in accordance with claim 13 wherein said cylinder is fused to the end of said core, and said cap is fused to said reflector.

17. A side firing fiberoptic probe in accordance with claim 13 wherein said cap has a spheroidal closed end portion.

* * * * *